US00PP29589P2

(12) United States Plant Patent
van den Hoogen

(10) Patent No.: US PP29,589 P2
(45) Date of Patent: Aug. 14, 2018

(54) ***ORIGANUM* PLANT NAMED 'ALL120506'**

(50) Latin Name: ***Origanum vulgare* L.**
Varietal Denomination: ALL120506

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 3 days.

(21) Appl. No.: 15/530,479

(22) Filed: Jan. 20, 2017

(51) Int. Cl.
*A01H 5/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
(74) *Attorney, Agent, or Firm* — C. A. Whealy

(57) ABSTRACT

A new and distinct cultivar of *Origanum* plant named 'ALL120506', characterized by its upright plant habit; moderately vigorous to vigorous growth habit; strong stems; relatively large leaves; early and freely flowering habit; light purple-colored flowers; and long flowering period.

2 Drawing Sheets

Botanical designation: *Origanum vulgare* L.
Cultivar denomination: 'ALL120506'.

BACKGROUND OF THE INVENTION

The present invention relates to a new and distinct cultivar of *Origanum* plant, botanically known as *Origanum vulgare* L., typically grown as a garden plant and hereinafter referred to by the name 'ALL120506'.

The new *Origanum* plant is a product of a planned breeding program conducted by the Inventor in Cuijk, The Netherlands. The objective of the breeding program is to create new strong *Origanum* plants with attractive flowers and early flowering habit.

The new *Origanum* plant originated from an open-pollination in June, 2011 of a proprietary selection of *Origanum vulgare* L. identified as code number 36-2010-3-2, not patented, as the female, or seed, parent with an unknown selection of *Origanum vulgare* L., as the male, or pollen, parent. The new *Origanum* plant was discovered and selected by the Inventor as a single flowering plant from within the progeny of the stated open-pollination grown in a controlled nursery environment in Cuijk, The Netherlands in July, 2013.

Asexual reproduction of the new *Origanum* plant by divisions in Cuijk, The Netherlands, since August, 2013 has shown that the unique features of this new *Origanum* plant are stable and reproduced true to type in successive generations.

SUMMARY OF THE INVENTION

Plants of the new *Origanum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ALL120506'. These characteristics in combination distinguish 'ALL120506' as a new and distinct *Origanum* plant:

1. Upright plant habit.
2. Moderately vigorous to vigorous growth habit.
3. Strong stems.
4. Relatively large leaves.
5. Early and freely flowering habit.
6. Light purple-colored flowers.
7. Long flowering period.

Plants of the new *Origanum* differ primarily from plants of the female parent selection in the following characteristics:

1. Plants of the new *Origanum* have stronger stems than plants of the female parent selection.
2. Plants of the new *Origanum* are more freely flowering than plants of the female parent selection.

Plants of the new *Origanum* can be compared to plants of *Origanum laevigatum* 'Rosenkuppel', not patented. In side-by-side comparisons plants of the new *Origanum* differ from plants of 'Rosenkuppel' in the following characteristics:

1. Plants of the new *Origanum* are taller than plants of 'Rosenkuppel'.
2. Plants of the new *Origanum* have broader leaves than plants of 'Rosenkuppel'.

BRIEF DESCRIPTION OF THE PHOTOGRAPHS

The accompanying colored photographs illustrate the overall appearance of the new *Origanum* plant showing the colors as true as it is reasonably possible to obtain in colored reproductions of this type. Colors in the photographs may differ slightly from the color values cited in the detailed botanical description which accurately describe the actual colors of the new *Origanum* plant.

The photograph on the first sheet is a side perspective view of a typical flowering plant of 'ALL120506'.

The photograph at the top of the second sheet is a close-up view of the upper (right) and lower (left) surfaces of typical leaves of 'ALL120506'.

The photograph at the bottom of the second sheet is a close-up view of a typical flowering plant of 'ALL120506'.

DETAILED BOTANICAL DESCRIPTION

The aforementioned photographs and following observations, measurements and values describe plants grown the autumn in 23-cm containers in an outdoor nursery in Rijswijk, The Netherlands and under cultural practices typical of commercial *Origanum* production. During the production of the plants, day temperatures ranged from 12° C. to 26° C. and night temperatures ranged from 4° C. to 16° C. Plants were 17 months old when the photograph and the description were taken. In the detailed description, color references are made to The Royal Horticultural Society Colour Chart, 2015 Edition, except where general terms of ordinary dictionary significance are used.

Botanical classification: *Origanum vulgare* L. 'ALL120506'.

Parentage:

*Female, or seed, parent*.—Proprietary selection of *Origanum vulgare* L. identified as code number 36-2010-3-2, not patented.

*Male, or pollen, parent*.—Unknown selection of *Origanum vulgare* L., not patented.

Propagation:

*Type cutting*.—By terminal cuttings.

*Time to initiate roots, summer*.—About 10 to 14 days at temperatures ranging from 12° C. to 30° C.

*Time to produce a rooted young plant, summer*.—About four to six weeks at temperatures ranging from 12° C. to 30° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density to dense.

Plant description:

*Plant and growth habit*.—Herbaceous perennial; upright plant form; moderately vigorous to vigorous growth habit; moderate growth rate.

*Plant height, soil level to top of foliar plane*.—About 43.5 cm.

*Plant height, soil level to top of floral plane*.—About 49.6 cm.

*Plant width*.—About 46.2 cm.

*Lateral branch description*.—Branching habit: Freely basal branching habit with about 23 primary branches, each with about four lateral branches. Length: About 6.6 cm. Diameter: About 2 mm. Internode length: About 2.8 cm. Strength: Strong. Aspect: Basal branches, mostly upright; lateral branches, about 60° from basal branches. Texture and luster: Densely pubescent; slightly glossy. Color, developing: Close to between 145A and 147D. Color, developed: Close to 145B tinged with close to 187A to 187C.

Leaf description:

*Arrangement*.—Opposite, simple.

*Length*.—About 3.3 cm.

*Width*.—About 2.7 cm.

*Shape*.—Broadly ovate.

*Apex*.—Broadly and bluntly acute to obtuse.

*Base*.—Short acuminate.

*Margin*.—Entire.

*Texture and luster, upper surface*.—Sparsely pubescent; matte.

*Texture and luster, lower surface*.—Moderately pubescent; matte.

*Venation pattern*.—Pinnate.

*Fragrance*.—Strongly aromatic; pleasant, spicy.

*Color*.—Developing and fully expanded leaves, upper surface: Close to 137B; venation, close to 137B. Developing and fully expanded leaves, lower surface: Close to 138B; venation, close to 138D.

*Petioles*.—Length: About 1.6 cm. Diameter: About 1.5 mm. Strength: Strong. Texture and luster, upper surface: Moderately pubescent; matte. Texture and luster, lower surface: Moderately pubescent; very slightly glossy. Color, upper surface: Close to 146D. Color, lower surface: Slightly lighter than 146D.

Flower description:

*Flower form, arrangement and flowering habit*.—Single labiate flowers arranged in terminal and axillary compound cymes; flowers face upright to somewhat outwardly; freely flowering habit with about 100 flowers developing per inflorescence and about 1,100 flowers developing per plant during the flowering season.

*Natural flowering season*.—Plants begin flowering about 13 weeks after planting; long flowering habit, plants flower from late spring into the late summer in The Netherlands.

*Postproduction longevity*.—Flowers maintain good substance for about one week on the plant; flowers not persistent.

*Fragrance*.—None detected.

*Flower buds*.—Length: About 7 mm. Diameter: About 2 mm. Shape: Obovate. Texture and luster: Sparsely pubescent; matte. Color: Close to NN74D and 75C; towards the apex, close to 177A; immature calyx, close to 145C.

*Inflorescence height*.—About 3.3 cm.

*Inflorescence diameter*.—About 3.9 cm.

*Flower length* (*vertical*).—About 5 mm.

*Flower diameter* (*horizontal*).—About 6 mm.

*Flower depth* (*height*).—About 1.4 cm.

*Petals*.—Arrangement: Labiate; upper lip, two-lobed; lower lip, three-lobed; lips fused 70% of total length. Length, upper lip: About 9 mm. Length, lower lip: About 1 cm. Width, upper lip: About 4 mm. Width, lower lip: About 6 mm. Shape, upper and lower lips: Oblanceolate; lobe apices, obtuse; margin, entire. Texture and luster, upper and lower lips, upper surface: Smooth, glabrous; matte. Texture and luster, upper and lower lips, lower surface: Moderately pubescent; matte. Color, upper and lower lips: When opening and fully opened, upper surface: Close to 75A to 75B; color does not fade with development. When opening and fully opened, lower surface: Close to 75A to 75B; color does not fade with development.

*Sepals*.—Quantity and arrangement: Five in a single whorl; lower 62.5% fused into a tubular calyx. Length: About 1 cm. Width: About 0.8 mm. Shape:

Narrowly oblong. Apex: Acute. Margin: Free parts, entire. Texture and luster, upper surface: Mostly smooth, glabrous; upper edge of tube, pubescent; matte. Texture and luster, lower surface: Smooth, glabrous; very slightly glossy. Color: When opening, upper and lower surfaces: Close to 145C; towards the apex, close to 177A. Fully opened, upper and lower surfaces: Close to 145C; towards the apex, close to 177B.

*Inflorescence bracts*.—Quantity and arrangement: One at the base of each flower. Length: About 7 mm. Width: About 3 mm. Shape: Obovate; apex, acute; base, attenuate. Margin: Entire. Texture and luster, upper and lower surfaces: Smooth, glabrous; very slightly glossy. Color, when opening and fully opened, upper surface: Close to 197B to 197D. Color, when opening and fully opened, lower surface: Slightly lighter than between N77A and 187B.

*Peduncles*.—Length: About 2.2 cm. Diameter: About 1.5 mm. Strength: Strong. Aspect: Mostly erect. Texture and luster: Densely pubescent; moderately glossy. Color: Close to 187C.

*Pedicels*.—Length: About 0.8 mm. Diameter: About 0.5 mm. Strength: Moderately strong. Aspect: About 22.5° from peduncle axis. Texture and luster: Smooth, glabrous; slightly glossy. Color: Close to 199B.

*Reproductive organs*.—Stamens: Quantity per flower: Four. Filament length: About 6.5 mm. Filament color: Close to 75B. Anther length: About 0.5 mm. Anther shape: Reniform. Anther color: Close to N186C. Pollen amount: Scarce. Pollen color: Close to N155A. Pistils: Quantity per flower: One. Pistil length: About 1 cm. Stigma diameter: About 0.5 mm. Stigma shape: Cleft. Stigma color: Close to N75A. Style length: About 1 mm. Style color: Close to 75A; towards the base, close to 75D. Ovary color: Close to 144B.

*Seed and fruit*.—Seed and fruit production have not been observed on plants of the new *Origanum*.

Disease & pest resistance: Plants of the new *Origanum* not been observed to be resistant to pathogens and pests common to *Origanum* plants.

Garden performance: Plants of the new *Origanum* have exhibited to tolerate rain, wind and high temperatures about 40° C.; and plants are suitable for USDA Hardiness Zones 5 to 10.

It is claimed:

1. A new and distinct *Origanum* plant named 'ALL120506' as illustrated and described.

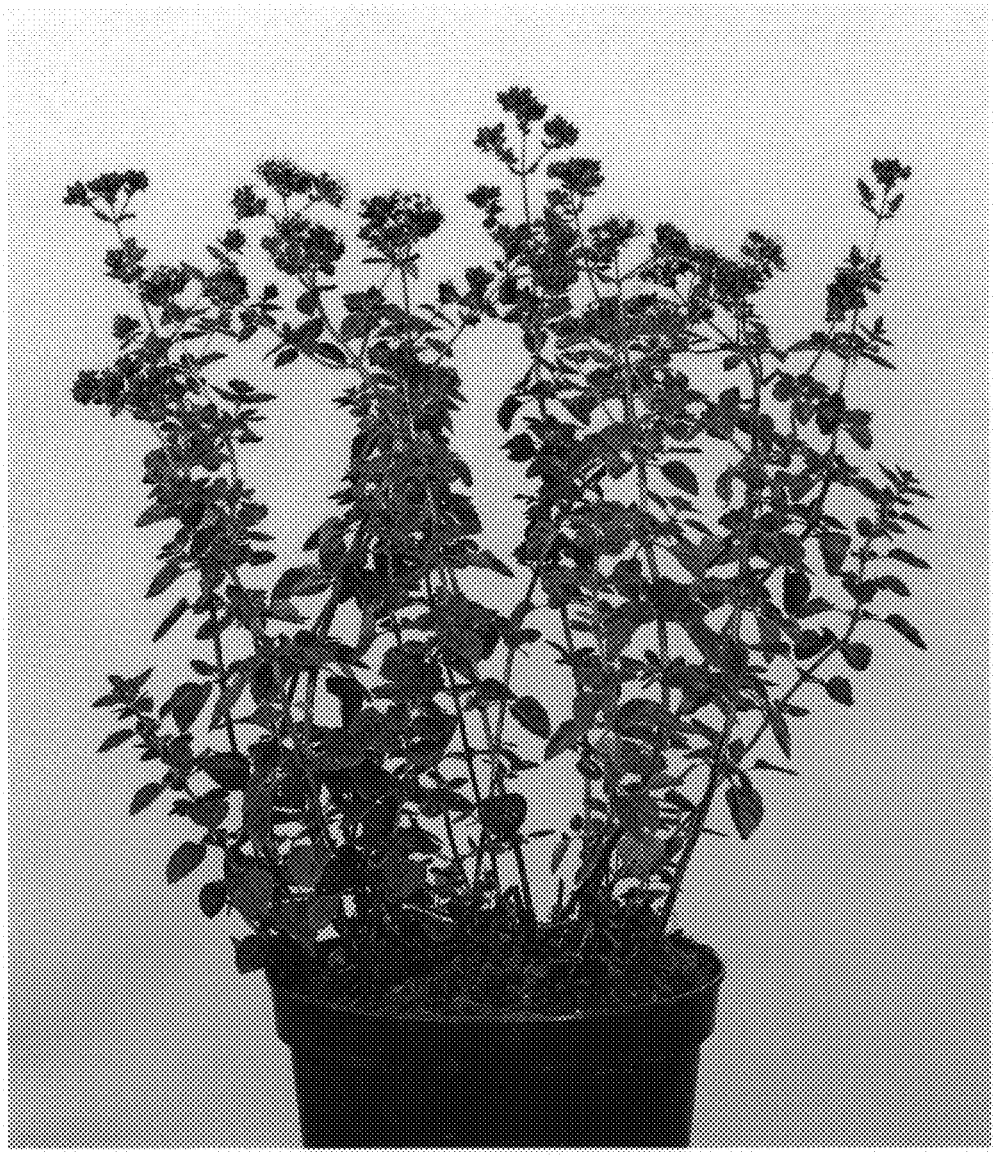

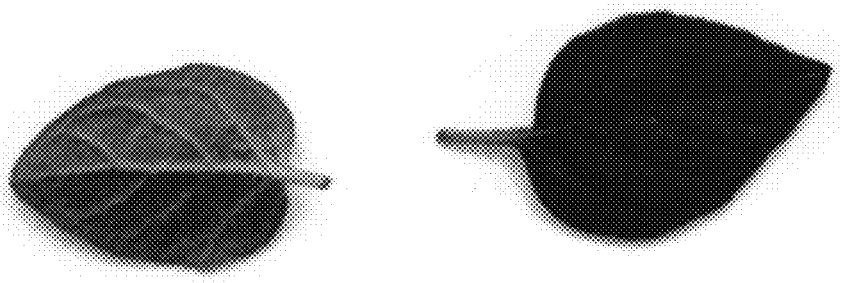
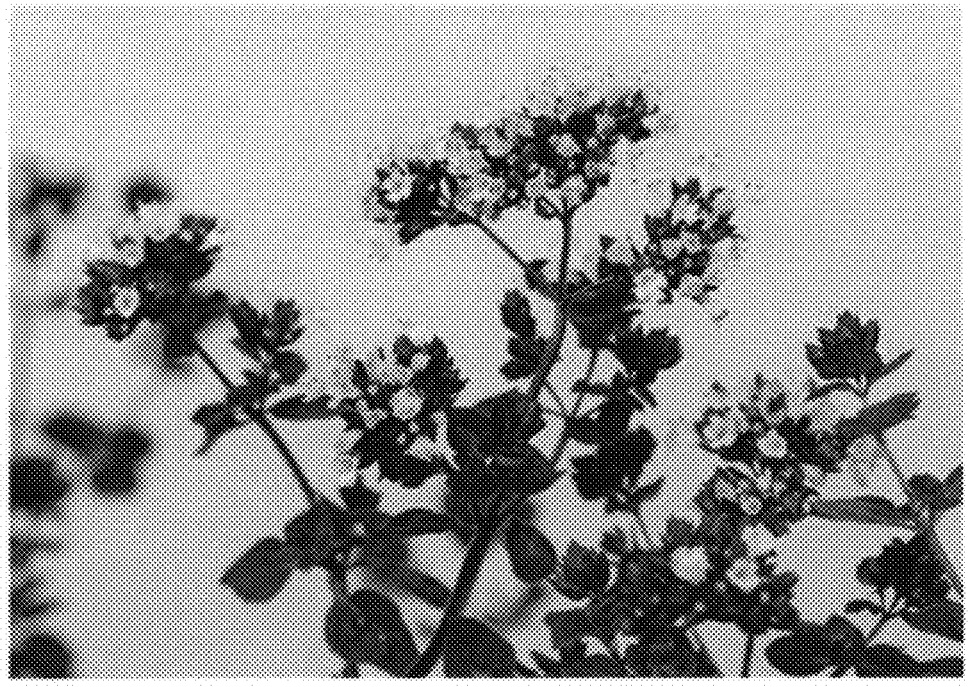

* * * * *